United States Patent [19]

Tomioka et al.

[11] 4,374,936
[45] Feb. 22, 1983

[54] LIQUID OF ACRYLIC COPOLYMER AND TETRAHYDROFURANTETRACARBOXYLIC ACID FOR SETTING DENTAL CEMENTS

[75] Inventors: Kentaro Tomioka, Chofu; Kazuo Hirota, Tokyo; Hiroaki Muramatsu, Gotenba; Shoji Akahane, Tokyo, all of Japan

[73] Assignee: G-C Dental Industrial Corp., Tokyo, Japan

[21] Appl. No.: 263,724

[22] Filed: May 14, 1981

[30] Foreign Application Priority Data

Jun. 4, 1980 [JP] Japan .................... 55-74409

[51] Int. Cl.³ .............................. C08K 5/09
[52] U.S. Cl. .................. 523/116; 525/386
[58] Field of Search ........... 523/109, 116; 525/256, 525/386

[56] References Cited

U.S. PATENT DOCUMENTS

| | | | |
|---|---|---|---|
| 3,804,794 | 4/1974 | Schmitt et al. | 523/116 |
| 3,856,737 | 12/1974 | Foster et al. | 523/116 |
| 4,089,830 | 5/1978 | Tezuka et al. | 523/116 |
| 4,222,920 | 9/1980 | Crisp et al. | 523/116 |

FOREIGN PATENT DOCUMENTS 2028855  3/1980  United Kingdom ........... 523/116

*Primary Examiner*—Joseph L. Schofer
*Assistant Examiner*—N. Sarofin
*Attorney, Agent, or Firm*—Oblon, Fisher, Spivak, McClelland & Maier

[57] ABSTRACT

A liquid for setting dental cements is provided, in which an aqueous solution of a copolymer of acrylic and maleic acids contains a tetrahydrofurantetracarboxylic acid alone or in combination with at least one of tartaric acid, a fluorocomplex salt and a specific organic carboxylic acid. The specific organic carboxylic acid is expressed by the general formula:

$$C_mH_n(COOH)_x(OH)_y$$

8 Claims, No Drawings

LIQUID OF ACRYLIC COPOLYMER AND TETRAHYDROFURANTETRACARBOXYLIC ACID FOR SETTING DENTAL CEMENTS

BACKGROUND OF THE INVENTION

The present invention is generally concerned with improvements in or relating to dental cements, among others, glass ionomer cements. In particular, it pertains to a novel liquid for setting dental cements which excells markedly in crushing strength, water resisting property and manipulation characteristics during mixing.

The glass ionomer cements that have main use in dentistry are prepared by setting reaction of fluoroaluminosilicate glass and a polycarboxylic acid such as polyacrylic acid under the presence of water, and their appearance is good thanks to the transparency of the glass mixed-in. In particular, the cements of this type have little or no detrimental corrosive or other harmful pathological action upon the pulp, exhibit satisfactory adhesion to both teeth, dentin and enamel, excel in marginal sealing property and maintain their resistance to the mouth tissues or fluids over an extended period of time. Owing to their unique capabilities, from which is free the commercially available composite resin of the resin type, the glass ionomer cements find important use as restorations for anterior teeth and as binders for prostheses, other linings or building-up. However, the glass ionomer cements which comprises a mere combination of an aqueous solution of polyacrylic acid and powders of fluoroaluminosilicate glass have now been found to be disadvantageous in that they provide a mixed product which is inferior in fluidity and manipulation characteristics, and takes a longer period of time for setting. As a result, the mixed product comes at its surface into contact with the oral fluids and disintegrates to such an extent that it becomes brittle, thus resulting in a lowering of the final strength. Laid-open Japanese Patent Application No. 101893/1977 specification discloses a process that does not offer such problems, and yet has advantages over the prior art. According to this process, 7 to 25% by weight of one or more of polybasic carboxylic acids are added to a 45 to 60% by weight aqueous solution of polyacrylic acid to prepare a setting liquid. In fact, this liquid is easy to manipulate so that setting is complete within a short period of time, and gives rise to increases in strength. When used as fillings for oral restorations, however, the setting cement as referred to above is susceptible to the mouth fluids and humidity, and has a cloudy tendency. For this reason, it is ordinarily required to apply a waterproofing treatment which comprises coating a waterproof varnish on the surface of the mixed product followed by sufficient drying, to thereby form a waterproof film. These procedures are tolerably troublesome and time-consuming as compared with the manipulation for filling the composite resin for the dental restoration.

As a consequence of extensive and intensive studies made concerning the polymer acid components and the additives with the intention of providing a solution to the above-mentioned problems, it has now surprisingly been found that a novel glass ionomer cement, which excels markedly in strength, enables a setting reaction to proceed rapidly, and is superior in water resisting property, is obtained by using a copolymer of acrylic acid and maleic acid, that is now proved to be best suited for use as the polymer acid in a setting liquid, and adding thereto a tetrahydrofurantetracarboxylic acid alone or in combination with at least one of tartaric acid, a fluorocomplex salt and a specific organic carboxylic acid.

As the powder for dental cements used in combination with the setting liquid according to the present invention, preference is given to the powders formulated by pulverization of the so-called fluoroaluminosilicate glass prepared by blending together 37 to 45% by weight of silicic anhydride, 25 to 35% by weight of aluminum oxide, 5 to 13% by weight of calcium oxide, 10 to 15% by weight of soda fluoride and 3 to 7% by weight of calcium phosphate and firing the resultant blend at about 1300° C. In analogy with a dental silicophosphate cement powder, however, no difficulty will be encountered in mixing the above-mentioned powder with the powder for a zinc phosphate cement obtained by firing of blending ingredients consisting mainly of 90 parts by weight of zinc oxide and 10 parts by weight of magnesium oxide. According to the present invention, a copolymer of acrylic acid, particularly of acrylic and maleic acid, is preferably used as the polymer acid. Preferably, the acrylic acid amounts to 60% or more in the copolymer.

The copolymer of acrylic acid and maleic acid according to the present invention has preferably a mean molecular weight of no more than 30,000, particularly 20,000 to 5,000. The molecular weight may be adjusted by selection of a polymerization regulator having a proper chain transfer constant, such as isopropyl alcohol, dodecyl mercaptane, thioglycolic acid, etc.

The term "mean molecular weight" used herein shall be determined on the basis of viscosity measurement according to the following calculating procedures: An intrinsic viscosity n is measured in a 2 N aqueous solution of caustic soda at 25° C., and an average molecular weight M is computed from the Sakamoto's empirical equation.

$$[\eta] = 1.21 \times 10^{-3} \times M^{0.54} (100 \text{ ml/g, } 25° \text{ C.})$$

(This equation is cited from a publication "The Journal of the Chemical Society of Japan" 83 386 (1962)).

In the present invention, it should be noted that the organic carboxylic acid used is chosen from a specifically limited range that is found to have the greatest effects on the properties of the improved glass ionomer, particularly on improvements in the manipulation characteristics, crushing strength and water resisting properties of the cement, when used in combination with the tetrahydrofurantetracarboxylic acid and the copolymer of acrylic acid and maleic acid. That is to say, the organic carboxylic acid to be used in the present invention should be selected from the compounds consisting of only a combination of C, H and O, having a structure comprising six or less skeletal carbon atoms to which relative carboxyl groups are bonded directly, as expressed by the general formula:

wherein m, n, x and y stand for integers on condition that m=1-6, n=0-6, x=m/2-6 (m: an even number) or [(m+1)/2]-6 (m: an uneven number), and y=0-1, and having in its skeleton at most one methylene group (—CH$_2$—) but neither other groups nor any double bonds that are soluble and easily polymerizable.

In other words, the organic carboxylic acid ranges from a monobasic to a polybasic acid containing six or less functional groups, since it has one to six skeletal carbon atoms and one to six relative carboxyl groups, correspondingly. Due to the need of at least one skeletal carbon atom, however, formic acid and oxalic acid, both free from any skeletal carbon atoms, are ruled out. Maleic, itaconic, citraconic or the like acid is also excluded from the present invention, since the specific carboxylic acid is required to resist substantially to polymerization and contain no ordinary double bond. In addition, any carboxylic acid containing in its skeleton two or more methylene groups or two or more OH groups attached directly to the skeletal carbon atoms or other groups cannot be applied; hence, glycolic acid is only a possible monobasic acid. Only a pertinent straight-chain dibasic acid is normally malonic acid, and dibasic acids containing two or more methylene groups such as succinic, glutaric, adipic, pimelic and suberic acids or those containing other substituents such as monoalkyl or dialkyl malonic and citric acids are ruled out. Tartaric or dehydrotartaric acid containing two or more OH groups does not also fall under the purview of the present invention. Methanetetraacetic acid, and ethylenediaminotetraacetic acid or nitrilotriacetic acid containing a nitrogen atom and two or more methylene groups are unsuitable for the purpose of the present invention.

If the number of the skeletal carbon atoms is m, then the number of the carboxyl groups attached directly thereto is in such a range as defined by $(m/2)-6$ or $[(m+1)/2]-6$ wherein m is an uneven number. This signifies that, if m represents 1, 2, 3, 4, 5 and 6, then the minimum number of the carboxyl groups attached directly to the skeletal carbon atoms is limited to 1, 1, 2, 2, 3 and 3, respectively. Consequently, the organic carboxylic acid defined hereabove contains one to six, two to six, and three to six —COOH groups relative to $C_1$ and $C_2$, $C_3$ and $C_4$, and $C_5$ and $C_6$, respectively. The allowable number of —$CH_2$— and —OH attached to each individual skeletal carbon is 1 or less. The organic carboxylic acids, that meet the above-mentioned requirements and can be used in the present invention, include, for example, methanetetracarboxylic, carboxymalonic, tartronic, malonic, glycolic ($C_1$), cyclopropanetricarboxylic, cyclopropanedicarboxylic ($C_3$), cyclopentanetetracarboxylic ($C_5$), benzenhexacarboxylic benzenepentacarboxylic and benzenetetracarboxylic ($C_6$) acids.

The tetrahydrofurantetracarboxylic acid used in the present invention is preferably tetrahydrofuran-2, 3, 4, 5-tetracarboxylic acid.

The tetrahydrofurantetracarboxylic acid alone or in combination with tartaric acid and/or at least one of the above-mentioned carboxylic acids should preferably be added in amounts ranging from 10 to 30% based on the total weight.

Simultaneous addition of the fluorocomplex salts in amounts of 0.1 to 5% gives rise to further improvements in the crushing strength of the cement.

The fluorocomplex salts effectively used in the present invention include, for instance, potassium tetrafluoroberyllate, ammonium tetrafluoroberyllate, sodium hexafluorozirconate, potassium hexafluorozirconate, potassium heptafluoroniobate, potassium heptafluorotantalate, sodium hexafluorosilicate, potassium hexafluorosilicate, litium hexafluorosilicate, ammonium hexafluorosilicate, iron hexafluorosilicate, nickel hexafluorosilicate, zinc hexafluorosilicate, tin hexafluorosilicate, magnesium hexafluorosilicate, manganese hexafluorosilicate, sodium hexafluorotitanate, potassium hexafluorotitanate, ammonium hexafluorotitanate, nickel hexafluorotitanate, potassium tetrafluoroborate, ammonium tetrafluoroborate, manganese tetrafluoroborate, iron tetrafluoroborate, nickel tetrafruoroborate, tin tetrafluorobotate, indium tetrafluoroborate, zinc tetrafluoroborate, antimony tetrafluoroborate, boron trifluoride-acetate complex and so on. Most preferable fluorocomplex salts are potassium tetrafluoroberyllate, sodium hexafluorozirconate, potassium hexafluorozirconate, sodium hexafluorosilicate, potassium hexafluorosilicate, zinc hexafluorosilicate, magnesium hexafluorosilicate, sodium hexafluorotitanate, potassium hexafluorotitanate and ammonium hexafluorotitanate.

These complex salts have a marked effect even in small quantities, but the amount of dissolution thereof in a polymer solution is generally limited owing to their less solubility. In addition, they exert a slight effect on increases in strength, even if they are added in larger amounts. For this reason, the amounts of the fluorocomplex salts added to the copolymer of acrylic acid and maleic acid range from 0.1 to 5% by weight, more preferably 0.1 to 3% by weight.

In principle, the fluorocomplex salts should be added directly to a copolymer solution. Due to their less solubility, however, there is a possibility that they may be dispersed in and mixed with dental cement powder composed mainly of the fluoroaluminosilicate glass, if necessary. The fluorocomplex salt powder added to the dental cement powder should have been finely divided such that they can pass through a 400-mesh sieve. 0.1 to 10% by weight, preferably 0.1 to 6% by weight of such powder is then added to and dispersed in the cement powder under mixing. The obtained product is mixed with the setting liquid, the composition of which is given below, to thereby form a mixed product which may be used as a dental cement. The objects of the present invention are as follows:

1. A liquid for setting dental cements in which a 45 to 55% aqueous solution of a copolymer of acrylic acid and maleic acid contains a tetrahydrofurantetracarboxylic acid in an amount ranging from 10 to 30% based on the total weight.

2. A liquid for setting dental cements in which a 45 to 55% aqueous solution of a copolymer of acrylic acid and maleic acid contains a tetrahydrofurantetracarboxylic acid and at least one of fluorocomplex salts in amount ranging from 10 to 30% and 0.1 to 5%, respectively, based on the total weight.

3. A liquid for setting dental cements in which a 45 to 55% aqueous solution of a copolymer of acrylic acid and maleic acid contains a tetrahydrofurantetracarboxylic acid and at at least one of organic carboxylic acids that are compounds consisting of only a combination of C, H and O, having a structure comprising six or less skeletal carbon atoms to which relative carboxyl groups are bonded directly, as expressed by the general formula:

$$C_mH_n(COOH)_x(OH)_y$$

wherein m, n, x and y stand for integers on condition that m=1-6, n=0-6, x=(m/2)-6 (m: an even number) or [(m+1)/6]-6 (m: an uneven number), and y=0-1, and having in its skeleton at most one methylene group (—$CH_2$—) but neither other groups nor any double bonds that are soluble and easily polymerizable, in a total amount ranging from 10 to 30% based on the total weight.

4. A liquid for setting dental cements in which a 45 to 55% aqueous solution of a copolymer of acrylic acid and maleic acid contains a tetrahydrofurantetracarboxylic acid and at least one of organic carboxylic acids that are compounds consisting of only a combination of C, H and O, having a structure comprising six or less skeletal carbon atoms to which relative carboxyl groups are bonded directly, as expressed by the general formula:

$$C_mH_n(COOH)_x(OH)_y$$

wherein m, n, x and y stand for integers on condition that m=1-6, n=0-6, x=(m/2)-6 (m: an even number) or [(m+1)/2]-6 (m: an uneven number), and y=0-1, and having in its skeleton at most one methylene group (—CH$_2$—) but neither other groups nor any double bonds that are soluble and easily polymerizable, in a total amount ranging from 10 to 30% based on the total weight, and further contains fluorocomplex salts in amounts ranging from 0.1 to 5% based on the total weight.

5. A liquid for setting dental cements in which at 45 to 55% aqueous solution of a copolymer of acrylic acid and maleic acid contains a tetrahydrofurantetracarboxylic acid and tartaric acid in a total amount ranging from 10 to 30% based on the total weight.

6. A liquid for setting dental elements in which a 45 to 55% aqueous solution of a copolymer of acrylic acid and maleic acid contains a tetrahydrofurantetracarboxylic acid and tartaric acid in a total amount ranging from 10 to 30% based on the total weight, and further contains fluorocomplex salts in amounts ranging from 0.1 to 5% based on the total weight.

7. A luqid for setting dental cements in which a 45 to 55% aqueous solution of a copolymer of acrylic acid and maleic acid contains a tetrahydrofurantetracarboxylic acid, tartaric acid and at least one of organic carboxylic acids that are compounds consisting of only a combination of C, H and O, having a structure comprising six or less skeletal carbon atoms to which relative carboxyl groups are bonded directly, as expressed by the general formula:

$$C_mH_n(COOH)_x(OH)_y$$

wherein m, n, x and y stand for integers on condition that m=1-6, n=0-6, x=(m/2)-6 (m: an even number) or [(m+1)/2]-6 (m: an uneven number), and y=0-1, and having in its skeleton at most one methylene group (—CH$_2$—) but neither other groups nor any double bonds that are soluble and easily polymerizable, in a total amount ranging from 10 to 30% based on the total weight.

8. A liquid for setting dental cements in which a 45 to 55% aqueous solution of a copolymer of acrylic acid and maleic acid contains a tetrahydrofurantetracarboxylic acid tartaric acid and at least one of organic carboxylic acids that are compounds consisting of only a combination of C, H and O, having a structure comprising six or less skeletal carbon atoms to which relative carboxyl groups are bonded directly, as expressed by the general formala:

$$C_mH_n(COOH)_x(OH)_y$$

wherein m, n, x and y stand for integers on condition that m=1-6, n=0-6, x=(m/2)-6 (m: an even number) or [(m+1)/2]-6 (m: an uneven number), and y=0-1, and having in its skeleton at most one methylene group (—CH$_2$—) but neither other groups nor any double bonds that are soluble and easily polymerizable, in a total amount ranging from 10 to 30% based on the total weight, and further contains fluorocomplex salts in amounts ranging from 0.1 to 5% based on the total weight.

Likewise, the copolymer of acrylic acid and maleic acid, the tetrahydrofurantetracarboxylic acid, the tartaric acid and the specific organic carboxylic acid may wholly or partly be applied in the powdery form.

The glass ionomer cement uses the fluoroaluminosilicate glass as the powdery ingredient, and it is proved that considerable amount of fluorine passes into the dentin in an earlier stage when the cement paste obtained by mixing the cement powder with a solution of the copolymer of acrylic acid and maleic acid is brought into contact with the teeth, thus preventing effectively the initial corrosion thereof. The addition of the fluorocomplex salts enhances further such a preventing effect.

The present invention will now be elucidated with reference to the following examples and controls.

EXAMPLE 1-5 and CONTROLS 1-3

In an ordinal container (flask or beaker), given quantities of tetrahydrofurantetracarbosylic acid, tartaric acid, a fluorocomplex salt, and a specific organic carboxylic acid were added to an aqueous solution of a copolymer of acrylic acid and maleic acid having a predetermined concentration. The container was sufficiently shaked, plugged and allowed to stand for 3 to 5 days in a thermostatic chamber, to thereby prepare a colorless and transparent solution. In this way, four types of the setting liquid according to the present invention were formulated.

In controls, three types of the setting liquids the composition of which is specified in Table 1, were prepared in a similar way.

In the table, the bracketed figures refer to the average molecular weight of the acrylic-maleic acid copolymers used, which was determined according to the foregoing procedures.

1.0 gram of each of the setting liquids thus formulated was mixed with 1.4 grams of dental cement powder specified below for about 30 seconds. The resultant product was then measured on setting time, and crushing strength and solubility after the lapse of 24 hours in accordance with the procedures provided by JIS T6602.

Dental Cement Powder: manufactured by G. C. Dental Industrial Corp., and sold under the trade name of NEW LUSILEX.

This powder is formulated by heat treatment of starting materials consisting of 40% by weight of silica sand, 26% by weight of alumina, 12% by weight of soda fluoride, 15% by weight of lime carbonate and 7% by weight of lime phosphate at about 1300° C.

The results are set forth in Table 2 which also shows JIS T6602 standard concerning zinc phosphate cement.

TABLE 1

| Ex. No. | Composition of Setting Liquid |
|---|---|
| 1 | Copolymer of 95% acrylic acid and |

TABLE 1-continued

| Ex. No. | Composition of Setting Liquid | |
|---|---|---|
| | 5% maleic acid (7500) | 44.0% |
| | Pure water | 44.0 |
| | Tetrahydrofuran-2,3,4,5-tetracarboxylic acid | 12.0 |
| 2 | Copolymer of 90% acrylic acid and 10% maleic acid (5800) | 49.0% |
| | Pure water | 40.5 |
| | Tetrahydrofuran-2,3,4,5-tetracarboxylic acid | 10.0 |
| | Potassium hexafluorosilicate | 0.5 |
| 3 | Copolymer of 80% acrylic acid and 20% maleic acid (15200) | 36.0% |
| | Pure water | 43.0 |
| | Tetrahydrofuran-2,3,4,5-tetracarboxylic acid | 10.0 |
| | Tartaric acid | 10.0 |
| | Sodium hexafluorosilicate | 1.0 |
| 4 | Copolymer of 90% acrylic acid and 10% maleic acid (5800) | 45.0% |
| | Pure water | 43.0 |
| | Tetrahydrofurantetracarboxylic acid | 9.0 |
| | Tartronic acid | 3.0 |
| 5 | Copolymer of 95% acrylic acid and 5% maleic acid (7500) | 43.0% |
| | Pure water | 44.0 |
| | Tetrahydrofurantetracarboxylic acid | 9.0 |
| | Tartronic acid | 3.0 |
| | Sodium hexafluorotitanate | 1.0 |
| Control 1 | Copolymer of 90% acrylic acid and 10% maleic acid (5800) | 50.0% |
| | Pure water | 50.0 |
| Control 2 | Copolymer of 90% acrylic acid and 10% maleic acid (7500) | 47.0% |
| | Pure water | 50.0 |
| | Tartaric acid | 3.0 |

TABLE 2

| Ex. No. | Setting time in minutes | Crushing Strength in Kg/cm$^2$ | Solubility in % |
|---|---|---|---|
| 1 | 6.0 | 1490 | 0.6 |
| 2 | 6.0 | 1510 | 0.4 |
| 3 | 5.0 | 1650 | 0.3 |
| 4 | 5.5 | 1610 | 0.2 |
| 5 | 5.0 | 1600 | 0.2 |
| Control 1 | 12.0 | 820 | 1.0 |
| Control 2 | 10.5 | 1010 | 0.8 |
| JIS T6602 Standard | 4 ~ 8 | 700 or above | 0.2% or below |

The results as tabulated above indicate that the setting liquid of the present invention has a setting time ranging from 5 to 6 minutes which is most effective from the clinical viewpoint, and a crushing strength higher than the JIS standard by a factor of two or more.

While it is generally said that the glass ionomer cement possesses a solubility far greater than that of the zinc phosphate cement, the setting liquid of the present invention has turned out to give rise to considerable increases in solubility.

From a comparison with the Controls, it is also found that the tetrahydrofurantetracarboxylic acid has a marked effect.

1.0 gram of the setting liquid obtained in Example 1 or 4 was mixed with 2.2 grams of the aforesaid dental cement powder for 30 seconds. The resultant product was then measured on setting time, crushing strength after 24 hours, and solubility after the lapse of 7 days according to the procedures provided in JIS T6603. The results are given in Table 3 which also shows the test results of a silicate cement (W Corp.) (Control 3) and the JIS T6603 standard concerning it.

TABLE 3

| Ex. No. | Setting Time in minutes | Crushing Strength in Kg/cm$^2$ | Solubility in % |
|---|---|---|---|
| 6 | 4.0 | 2090 | 0.3 |
| 7 | 4.0 | 2770 | 0.2 |
| Control 3 | 3.5 | 1890 | 0.9 |
| JIS T6603 Standard | 3 ~ 8 | 1500 or above | 1.5% or below |

The results show that the crushing strength increases with the amount of the cement powder. A comparison of the examples and the control also indicates that the setting liquid of the present invention is superior in the manipulation characteristics due to its less solubility, and is most effective for the filling purpose.

What is claimed is:

1. A liquid for setting dental cements in which a 45 to 55% aqueous solution of a copolymer of acrylic acid and maleic acid contains a tetrahydrofurantetracarboxylic acid in an amount ranging from 10 to 30% based on the total weight.

2. A liquid for setting dental cements in which a 45 to 55% aqueous solution of a copolymer of acrylic acid and maleic acid contains a tetrahydrofurantetracarboxylic acid and at least one of fluorocomplex salts in amounts ranging from 10 to 30% and 0.1 to 5%, respectively, based on the total weight.

3. A liquid for settling dental cements in which a 45 to 55% aqueous solution of a copolymer of acrylic acid and maleic acid contains a tetrahydrofurantetracarboxylic acid and at least one of organic carboxylic acids that are compounds consisting of only a combination of C, H and O, having a structure comprising six or less skeletal carbon atoms to which relative carboxyl groups are bonded directly, as expressed by the general formula:

$$C_mH_n(COOH)_x(OH)_y$$

wherein m, n, x and y stand for integers on condition that m=1-6, n=0-6, x=(m/2)-6 (m: an even number) or [(m+1)/2]-6 (m: an uneven number), and y=0-1, and having in its skeleton at most one methylene group (—CH$_2$—) but neither other groups nor any double bonds that are soluble and easily polymerizable, in a total amount ranging from 10 to 30% based on the total weight.

4. A liquid for setting dental cements in which a 45 to 55% aqueous solution of a copolymer of acrylic acid and maleic acid contains a tetrahydrofurantetracarboxylic acid and at least one of organic carboxylic acids that are compounds consisting of only a combination of C, H and O, having a structure comprising six or less skeletal carbon atoms to which relative carboxyl groups are bonded directly, as expressed by the general formula:

$$C_mH_n(COOH)_x(OH)_y$$

wherein m, n, x and y stand for integers on condition that m=1-6, n=0-6, x=(m/2)-6 (m: an even number) or [(m+1)/2]-6 (m: an uneven number), and y=0-1, and having in its skeleton at most one methylene group (—CH$_2$—) but neither other groups nor any double bonds that are soluble and easily polymerizable, in a total amount ranging from 10 to 30% based on the total weight, and further contains fluorocomplex salts in amounts ranging from 0.1 to 5% based on the total weight.

5. A liquid for setting dental cements in which a 45 to 55% aqueous solution of a copolymer of acrylic acid and maleic acid contains a tetrahydrofurantetracarboxylic acid and tartaric acid in a total amount ranging from 10 to 30% based on the total weight.

6. A liquid for setting dental cements in which a 45 to 55% aqueous solution on a copolymer of acrylic acid and maleic acid contains a tetrahydrofurantetracarboxylic acid and tartaric acid in a total amount ranging from 10 to 30% based on the total weight, and further contains fluorocomplex salts in amounts ranging from 0.1 to 5% based on the total weight.

7. A liquid for setting dental cements in which a 45 to 55% aqueous solution of a copolymer of acrylic acid and maleic acid contains a tetrahydrofurantetracarboxylic acid, tartaric acid and at least one of organic carboxylic acids that are compounds consisting of only a combination of C, H and O, having a structure comprising six or less skeletal carbon atoms to which relative carboxyl groups are bonded directly, as expressed by the general formula:

$$C_mH_n(COOH)_x(OH)_y$$

wherein m, n, x and y stand for integers on condition that $m=1-6$, $n=0-6$, $x=(m/2)-6$ (m: an even number) or $[(m+1)/2]-6$ (m: an uneven number), and $y=0-1$, and having in its skeleton at most one methylene group ($-CH_2-$) but neither other groups nor any double bonds that are soluble and easily polymerizable, in a total amount ranging from 10 to 30% based on the total weight.

8. A liquid for setting dental cements in which a 45 to 55% aqueous solution of a copolymer of acrylic acid and maleic acid contains a tetrahydrofurantetracarboxylic acid, tartaric acid and at least one of organic carboxylic acids that are compounds consisting of only a combination of C, H and O, having a structure comprising six or less skeletal carbon atoms to which relative carboxyl groups are bonded directly, as expressed by the general formula:

$$C_mH_n(COOH)_x(OH)_y$$

wherein m, n, x and y stand for integers on condition that $m=1-6$, $n=0-6$, $x=(m/2)-6$ (m: an even number) or $[(m+1)/2]-6$ (m: an uneven number), and $y=0-1$, and having in its skeleton at most one methylene group ($-CH_2-$) but neither other groups nor any double bonds that are soluble and easily polymerizable, in a total amount ranging from 10 to 30% based on the total weight, and further contains fluorocomplex salts in amounts ranging from 0.1 to 5% based on the total weight.

* * * * *